United States Patent [19]
Ruff

[11] Patent Number: 5,482,038
[45] Date of Patent: Jan. 9, 1996

[54] NEEDLE ELECTRODE ASSEMBLY

[75] Inventor: Leonard H. Ruff, Kennewick, Wash.

[73] Assignee: Cadwell Industries, Inc., Kennewick, Wash.

[21] Appl. No.: 267,784

[22] Filed: Jun. 28, 1994

[51] Int. Cl.⁶ .................................................. A61B 5/0492
[52] U.S. Cl. ........................ 128/642; 439/482; 439/820; 439/909
[58] Field of Search .................................. 128/639, 642, 128/733, 735, 907; 607/116; 606/44, 45, 49, 185, 186, 187, 188, 189; 279/51; 439/482, 820, 909

[56] References Cited

U.S. PATENT DOCUMENTS

| | | | |
|---|---|---|---|
| 10,115 | 5/1882 | Phillips | 279/51 |
| 1,781,362 | 11/1930 | Brigida . | |
| 2,438,797 | 3/1948 | Bogge | 279/51 |
| 2,935,329 | 5/1960 | Hessler | 279/51 |
| 2,966,363 | 12/1960 | Hendrickson | 279/51 |
| 3,172,676 | 3/1965 | Kern, Jr. | 279/51 |
| 3,532,095 | 10/1970 | Miller et al. | 606/45 |
| 3,597,582 | 8/1971 | Goode et al. | 606/45 |
| 3,844,291 | 10/1974 | Moen | 279/51 |
| 4,091,880 | 5/1978 | Troutner et al. | 279/51 |
| 4,295,467 | 10/1981 | Mann et al. | 128/303.18 |
| 4,374,527 | 2/1983 | Iversen | 128/785 |
| 4,597,620 | 7/1986 | Lindner et al. | 339/89 |
| 4,633,880 | 1/1987 | Osypka et al. | 128/642 |
| 4,657,016 | 4/1987 | Garito et al. | 606/45 |
| 4,706,682 | 11/1987 | Stypulkowski et al. | 128/642 |
| 4,892,105 | 1/1990 | Prass | 128/741 |
| 4,998,934 | 3/1991 | Bernstein | 606/44 |
| 4,998,934 | 3/1991 | Bernstein | 606/44 |
| 5,170,788 | 12/1992 | Blumenfeld | 128/642 |
| 5,256,138 | 10/1993 | Burek et al. | 606/42 |

OTHER PUBLICATIONS

Miscellaneous Electrode Brochures, *Jari Electrode Supply*, Date Unknown.
Chan, Rai Chi et al., "Quantitative Comparison of Motor Unit Potential Parameters Between Monopolar and Concentric Needles", *Muscle & Nerve*, 14:1028–1032, 1991.

*Primary Examiner*—Lee S. Cohen
*Attorney, Agent, or Firm*—Christensen O'Connor Johnson & Kindness

[57] ABSTRACT

A holder (16) for releasably holding needle electrodes (18). The holder (16) includes a body (26) having a base slidably mounted within the body. Depressing the base into the body (26) releases a gripping assembly (50) located within the body (26) allowing a needle electrode (18) inserted into the holder to be removed. Releasing the base (24) causes the gripping assembly to engage a needle electrode inserted into the holder. The gripping mechanism (50) includes a chuck (60) having an opening sized to receive the needle electrode (18). The chuck engages a ferrule (73) that depresses the jaws (70) of the chuck (68) radially inwardly with respect to each other to reduce the size of the opening in the chuck thus holding a needle electrode (18) inserted into the chuck (68).

19 Claims, 3 Drawing Sheets

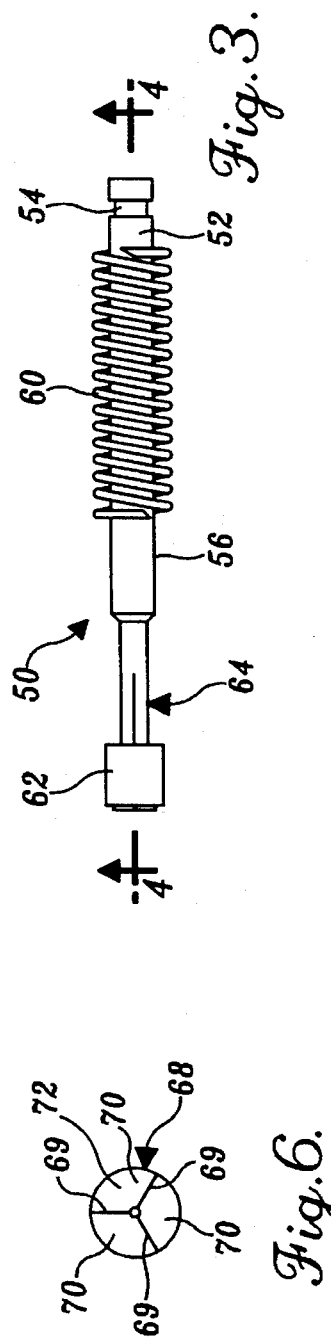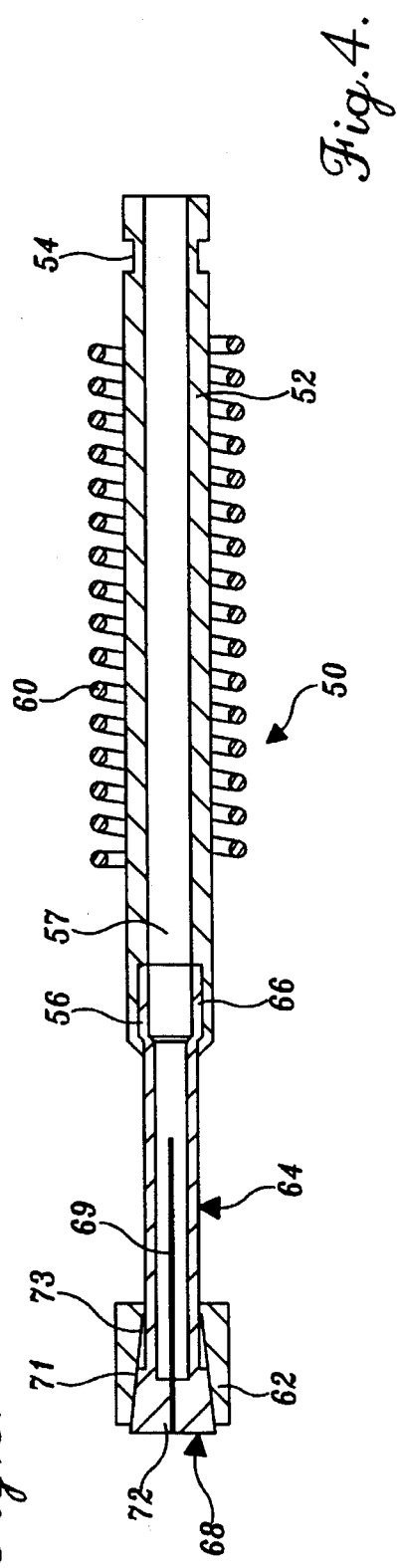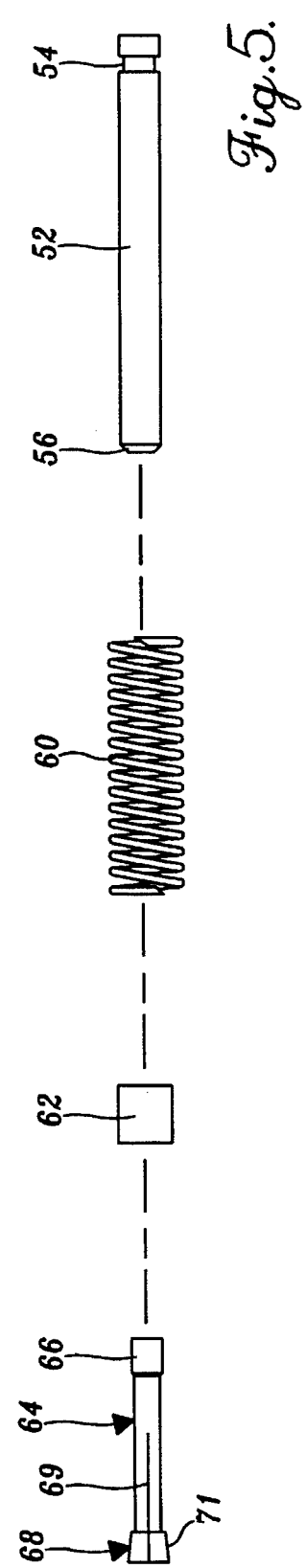

NEEDLE ELECTRODE ASSEMBLY

FIELD OF THE INVENTION

The present invention relates to needle electrode assemblies, specifically, the present invention relates to reusable needle electrode assemblies and holders.

BACKGROUND OF THE INVENTION

Needle electrodes are designed for use in neurological examinations using electronic monitoring equipment, namely electromyograph (EMG) equipment. The needle electrodes are connected to monitoring equipment and then inserted into a patient's muscle at the location that is to be stimulated or probed. As a needle electrode is inserted into a patient's body, both the electrode and operator may be exposed to bodily fluids carrying infectious diseases. Because of the danger associated with exposure to bodily fluids, the Food and Drug Administration (FDA) has stringent requirements regarding packaging, sterilization, reuse, disposal and testing performed using needle electrodes.

FDA requirements have resulted in two basic types of needle electrodes being used in the marketplace. The first type of needle electrode generally used is a disposable electrode assembly including needle electrode, lead wires, and electrical connectors all joined to form a single unit. The electrode assemblies are generally sterilized and prepackaged for a one-time use by a physician. The physician opens the sterilized package, connects the needle electrode to the appropriate monitoring equipment, and inserts the needle electrode into a patient's muscle. After completing testing, the entire electrode assembly is disconnected from the monitoring equipment and discarded.

Disposable needle electrode assemblies are fairly expensive and highly wasteful of resources due to their one-time use. Disposable electrode assemblies also add to the quantity of medical waste produced, increasing waste disposal costs. Because specific users require various length and diameter disposable needle electrode assemblies, users must stock large numbers of expensive needle electrode assemblies, adding to inventory overhead and storage costs.

The second type of needle electrode assembly commonly available is a reusable needle electrode assembly designed to be sterilized after each use. Similar to disposable assemblies, reusable needle electrode assemblies are generally manufactured as single piece units including electrical connectors, leads, and needle electrodes. Reusable needle electrode assemblies are not as wasteful of resources; however, they are expensive and time-consuming to use due to the procedures necessary to sterilize the needle electrode assemblies prior to each use. As with disposable needle electrode assemblies, reusable needle electrode assemblies are generally manufactured as a single unit having a needle electrode of a specified diameter and length, making it necessary for a physician to keep a large stock of various needle diameter and lengths on hand, adding to inventory and storage costs.

Some reusable needle electrode assemblies are designed with detachable needle electrodes. In such assemblies, an electrical housing and leads are formed as one unit and a needle electrode and an electrical connector used to connect the electrode to the leads are formed as a second unit.

It would be advantageous to have a needle electrode assembly that is reusable and does not require expensive and time-consuming sterilization procedures after each use. It would also be beneficial to have a needle electrode assembly that allows different sizes and lengths of needle electrodes to be releasably attached to electrical connectors and leads to reduce fabrication costs and allow physicians to stock various sizes and lengths of needle electrodes, as opposed to stocking various sizes of needle electrode assemblies.

The present invention is directed to reducing or eliminating some or all of the disadvantages of prior needle electrode assemblies discussed above.

SUMMARY OF THE INVENTION

In accordance with the present invention, a releasable and reusable needle electrode assembly for use with all types of neurological monitoring equipment is provided. The needle electrode assembly includes a holder capable of releasably holding needle electrodes of various sizes, shapes, and lengths. The needle electrode-holder of the present invention may be operated by placing the needle electrode holder in a single hand and then depressing the base of the holder to release or insert a needle electrode. The needle electrode is inserted into the tip of the needle electrode holder while depressing the base of the needle electrode holder. Upon releasing the base of the needle electrode holder, the internal engagement mechanism of the needle electrode holder engages and holds the needle electrode in place. The needle electrode holder is in turn connected to leads that are connected to neurological monitoring equipment.

One embodiment of the invention comprises a needle electrode assembly having a holder for releasably holding a needle electrode. The holder includes a body having a base slidably coupled to the body. A chuck is coupled to the base and includes an opening that is sized to receive and releasably hold a needle electrode. The chuck is adjustable between an engaged position in which the chuck engages a needle electrode and a released position in which the needle electrode may be freely removed by sliding the base with respect to the body.

According to other aspects of the invention, a biasing means biases the chuck into the engaged position in which the chuck holds the needle electrode. The chuck is moved into the engaged position through the use of a ferrule that at least partially encircles the chuck. Slidably moving the base with respect to the body causes the chuck to move at least partially into and out of the ferrule thus moving the jaws of the chuck radially inwardly and outwardly, enlarging or reducing the size of the opening in the chuck. The tip of the holder includes a conically-shaped opening that helps to guide the needle electrode into the opening in the chuck. The body of the holder is shaped such that it may be held between the thumb and two fingers of a user's hand during operation.

The needle electrode holder of the present invention allows a physician to purchase the required number of needle electrode holders and then purchase needle electrodes of various sizes and lengths. The needle electrodes may be releasably inserted into the needle electrode holder and subsequently discarded or sterilized depending upon the application. The needle electrode holder of the present invention may be used in combination with a needle electrode including a standoff mechanism that prevents the needle electrode holder from coming into contact with a patient's bodily fluid. Thus, the needle electrode holder of the present invention may be reused with different needle electrodes without being resterilized prior to every use. Use of the present invention should reduce medical costs by reducing the amount of medical waste that must be disposed of.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a side elevational view of the electrode gripping assembly of FIG. 2;

FIG. 4 is a cross-sectional view of the electrode gripping assembly of FIG. 3 along line 3—3;

FIG. 5 is an exploded view of the electrode gripping assembly of FIG. 3; and

FIG. 6 is an end elevational view of the three-jaw chuck of the electrode gripping assembly.

DETAILED DESCRIPTION OF THE PREFERRED EMBODIMENT

Figure 1:
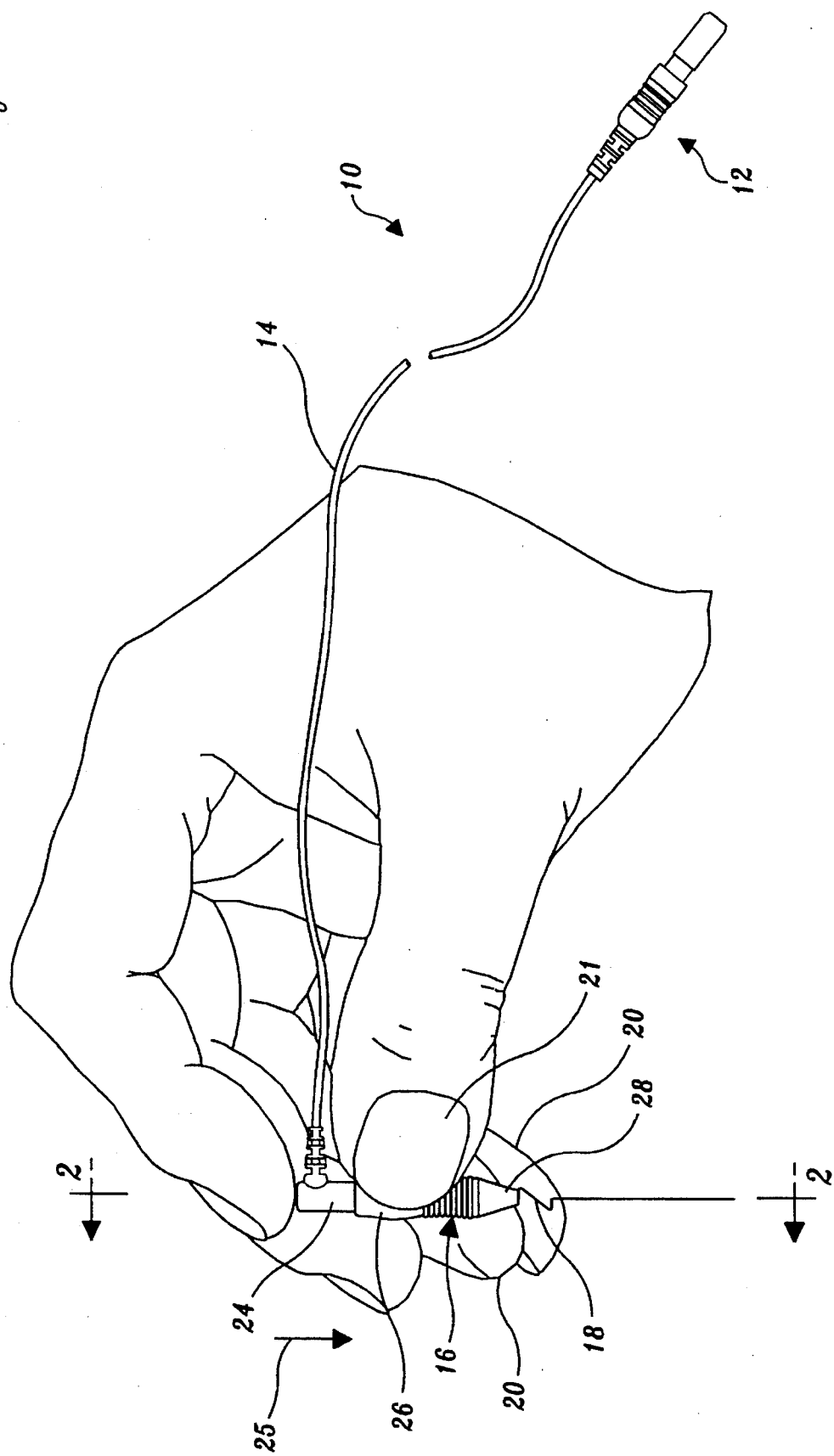
FIG. 1 is a side elevational view of the preferred embodiment of a needle electrode assembly according to the present invention.

The preferred embodiment of a needle electrode assembly 10 including a needle electrode holder 16 according to the present invention is illustrated in FIG. 1. The needle electrode assembly 10 includes an electrical connector 12 that is configured to connect to neurological monitoring equipment, namely EMG monitoring equipment (not shown). The electrical connector 12 is connected to one end of an electrical lead 14. The other end of the electrical lead 14 is connected to the needle electrode holder 16 as described in more detail below.

The needle electrode holder 16 is configured to releasably engage or disengage a needle electrode 18 that has been placed in the tip 28 of the needle electrode holder 16. The needle electrode holder 16 is configured to be held between the middle finger and thumb 21 of a user's hand and depressed with the index finger, as shown in FIG. 1. Depressing the base 24 of the needle electrode holder 16 in the direction of the arrow 25 causes the needle electrode holder to disengage, thus allowing the needle electrode 18 to be inserted into the conical tip 28 or to fall out of the tip as described in more detail below. Releasing the base 24 of the needle electrode holder 16 causes the needle electrode holder 16 to engage and grab a needle electrode 18 that has been inserted into the conical tip 28, thus holding the needle electrode for use during stimulation or probing.

Figure 2:
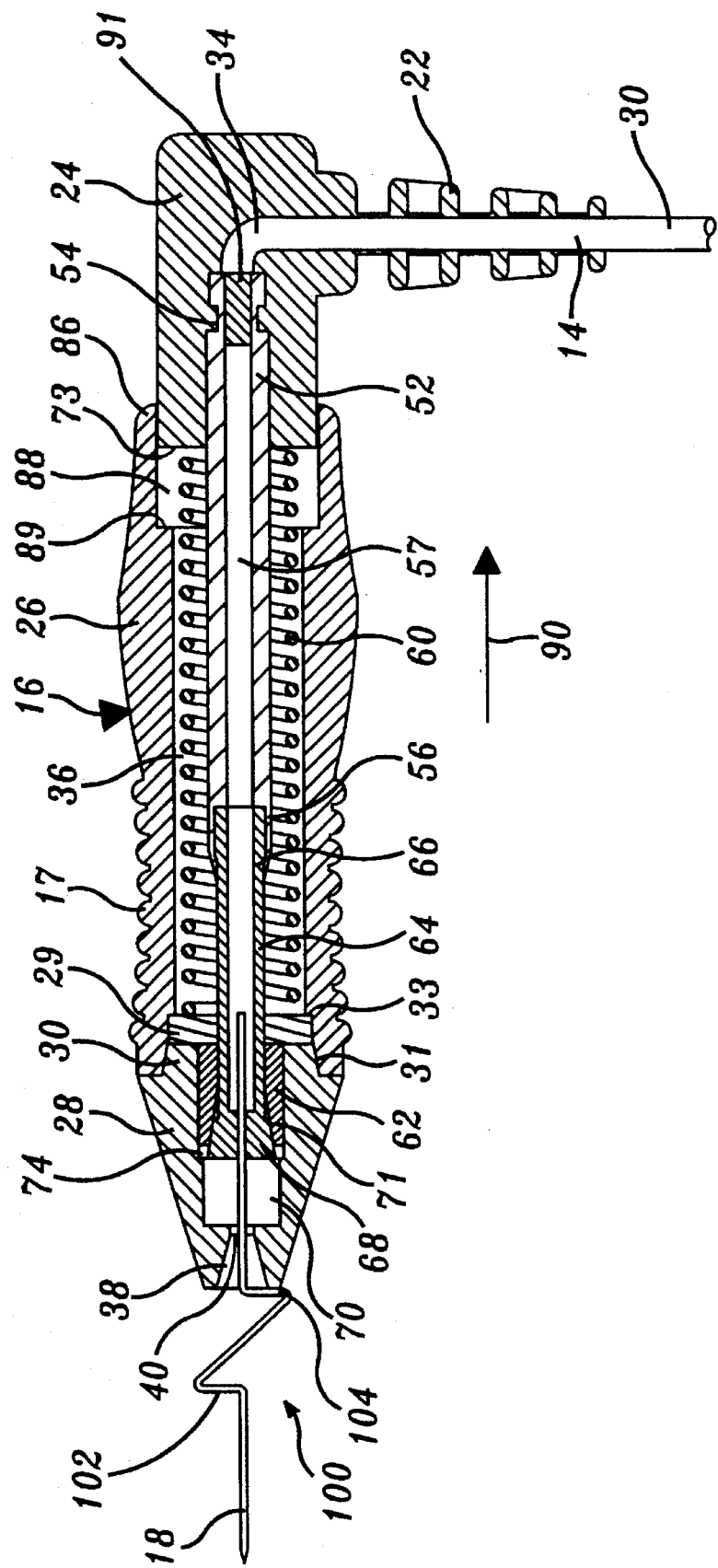
FIG. 2 is a cross-sectional view of the needle electrode holder of FIG. 1 along line 2—2.

As shown in FIGS. 1 and 2, the electrode holder 16 is generally formed of a base 24 that is slidably mounted within a body 20 having a cylindrical interior 36. A conical tip 28 is rigidly attached to the end of the body 16 opposite the base 24.

The base 24 includes a flexible lead retainer 22 that extends out one side of the base. The retainer 22 includes a central passageway 34 that is sized to receive the electrical lead 14. The flexible lead retainer 22 surrounds the electrical lead 14 and helps to prevent the electrical lead from being pulled away from the base 24, thus helping to prevent possible disconnection to the electrical lead.

The base 24 is slidably mounted within a cylindrical opening 88 in one end of the body 26 of the needle electrode holder 16. The conical tip 28 is rigidly attached to the opposite end of the body. The conical tip 28 includes a cylindrical protrusion 30 that extends rearwardly from the large diameter end of the conical tip. The cylindrical protrusion 30 is sized to extend into and engage the cylindrical interior wall 31 of the end of the body 26. The conical tip 28 is attached to the body 26 by adhesive bonding or another commonly known method of attachment, e.g., threading the cylindrical protrusion 30 of the conical tip 28 into the cylindrical interior wall 31 of the body 26. The smaller diameter end of the conical tip 28, which is located opposite the body 26, includes a conical opening 38 that has its largest diameter adjacent the end of the tip and its smallest diameter interior from the end of the tip. The smallest diameter end of the conical opening 38 opens into a hollow cylindrical interior 70 of the conical tip.

The base 24 is generally cylindrical and has an exterior diameter that is smaller than the interior diameter of the rear portion 86 of the body 26 such that the base is free to slide within a cylindrical opening 88 located at the rear of the body. Depressing the base 24 toward the body 26 causes the base to slidably move into the cylindrical opening 88. The distance the base 24 may move into the body 26 is limited by a shoulder 89 located at the forward end of the cylindrical opening 88. Releasing the base 24 results in the base being biased away from the body 26. The extent to which the base 24 may move away from the body while remaining within the cylindrical opening 88 is limited, as described below.

The inward and outward movement of the base 24 causes an electrode gripping assembly 50 (FIG. 3) located within the cylindrical interior 36 of the body 26 to releasably engage or disengage the needle electrode 18. The structure and operation of the electrode gripping assembly 50 is best shown by FIGS. 3–6. The electrode gripping assembly 50 includes a stem 52 that is connected at one end to a collet assembly 64. The stem 52 is a cylindrical tube having a recessed groove 54 extending around the circumference of the stem at the end of the stem opposite the collet assembly 64. Swaged connector 56 connects the other end of the stem to the collet assembly. In the preferred embodiment, the base 24 is formed of plastic that is injection molded around the end of the stem 52-opposite the collet assembly 64. The plastic resin forming the base 24 flows into the recessed groove 54 in the stem 52, helping to maintain the stem 52 rigidly within the base.

The collet assembly 64 is a cylindrical tube that includes a greater diameter raised portion 66 at the end of the collet assembly that is attached to the stem 52 by swaging. The raised portion 66 is sized to be received within an enlarged end of a passageway 57 that extends through the interior of the stem 52. After inserting the raised portion 66 of the collet assembly 64 into the passageway 57, the end 56 of the stem 52 is swaged over the raised portion 66 of the collet assembly (FIG. 4) in order to attach the stem to the collet assembly.

The end of the collet assembly 64 opposite the raised portion 66 includes a conical three-jaw split chuck 68. The split chuck 68 is formed by slitting the cylindrical collet assembly 64 lengthwise along three equally spaced apart slots 69. The slots start from the front of the split chuck 68 and extend partially along the cylindrical tube toward the band 66. Thus three separate pieces or jaws 70 are formed, as best seen in the end elevational view of the chuck shown in FIG. 6. The exterior surface 71 of each jaw 70 slopes outwardly from a point interior from the end of the collet assembly to form a conical shape having a greater diameter at the end of the split chuck than at a point interior from the end.

The split chuck 68 includes an internal passageway 72 that extends through the center of the collet assembly 64. The passageway 72 is sized so that the needle electrode 18 may be placed within the split chuck 68 and engaged by the jaws 70 of the split chuck when the jaws are compressed as described below. The slots 69 in the split chuck 68 are of a sufficient width to allow the needle electrode to be inserted into the passageway 71 when the jaws 70 are in an uncompressed position while allowing the jaws to engage and hold the needle electrode 18 when the jaws are in a compressed position as described below.

The jaws 70 of the split chuck 68 are compressed through the use of a cylindrical ferrule 62 that is placed around the exterior of the split chuck 68. The interior surface 73 (FIG. 4) of the cylindrical ferrule 62 is conical and shaped to mate with the sloped surface 71 of the split chuck 68 when the ferrule is placed over the split chuck, as best seen in FIG. 4.

As the cylindrical ferrule 62 is slidably moved toward the split chuck 68, the sloped interior surface 73 of the ferrule contacts the sloped exterior surface 71 of the split chuck. As the cylindrical ferrule 62 is moved further over the split chuck 68, the contact between the interior surface 73 of the cylindrical ferrule and the exterior surface 71 of the split chuck pushes the three jaws 70 radially inwardly, decreasing the diameter of the passageway 72 through the split chuck 68. As the three jaws 70 are pushed together, they contact and grip the end of the needle electrode 18 after it has been inserted into the passageway 72 as described below.

A cylindrical coil spring 60 is located around the exterior of the stem 52. The front end of the spring 60 contacts a retaining clamp 29, located in the electrode body 26 adjacent to the end of the cylindrical portions 30 of the conical tip 78, when the electrode gripping assembly 50 is placed within the electrode body. The opposite end of the spring 60 contacts a forward edge 73 of the base 24 after the electrode gripping assembly 50 has been placed with the electrode body 16. The spring 60 biases the base 24 away from the body 16 of the electrode holder such that the cylindrical ferrule 62 is maintained tightly around the split chuck 68, thus biasing the split chuck into an engaged position in which the jaws 70 of the chuck are forced together to engage a needle electrode 18 placed within the jaws.

The mechanical interaction between the electrode gripping assembly 50 and the body 16 and base 24 of the electrode holder will now be described with reference to FIG. 2. As discussed above, the stem 52 of the electrode gripping assembly 50 is rigidly attached to the base 24. The combined electrode gripping assembly 50 and base 24 are slidably mounted within the interior 36 of the body 26. Specifically, the base 24 slides freely within the cylindrical opening 88 formed in the rear end of the body 26. The stem 52 and collet assembly 64 extend through the interior 36 of the body 26 and into the cylindrical interior 70 of the tip 28.

The electrode gripping assembly 50 and, thus, the base 24 are prevented from moving rearwardly out of the body 26 by the retaining clamp 29, which encircles the collet assembly 64 just rearwardly of the ferrule 62. The retaining clamp 29 is inserted around the collet assembly 64 after the electrode gripping assembly 50 has been placed within the body 26 and before the conical tip 28 has been adhesively bonded to the front of the body. The retaining clamp 29 fits within the end of the body 26 opposite the end in which the base 24 is slidably mounted. The retaining clamp 29 is prevented from moving rearwardly past a predetermined position within the interior 36 of the body 26 by a narrow shoulder 33 formed in the interior surface of the body. The forward side of the clamp 29 serves as a rearward stop to prevent rearward movement of the ferrule 62 past a predetermined position, thus maintaining the electrode gripping assembly 50 within the body 26. As noted above, the rearward side of the retaining clamp 29 contacts the forward end of the biasing spring 60 thus allowing the biasing spring to bias the base 24 rearwardly away from the body 26.

The electrode gripping assembly 50 is movable from an engaged position in which the jaws 70 of the split chuck 68 are compressed to engage the needle electrode 18 to a disengaged position in which the jaws of the split chuck are not compressed, thus allowing the needle electrode 18 to be removed from the needle electrode holder 16. In the engaged position, the stem 52 and base 24 are biased rearwardly by spring 60 in the direction of the arrow 90 (FIG. 2), such that the rearward edge of the cylindrical ferrule 62 contacts the front side of the clamp 29, thus preventing the ferrule from moving rearwardly. The biasing force provided by the spring 60 continues to bias the collet assembly 64 rearwardly, forcing the exterior surfaces 71 of the split chuck 68 into contact with the interior surface 73 of the ferrule 62, thus forcing the jaws 70 together as described above.

The electrode gripping assembly 50 is released by depressing the base 24 inwardly toward the body 26 against the biasing force provided by the spring 60 such that the base 24 slidably moves within the cylindrical opening 88 in the direction opposite the arrow 90. As the base 24 moves into the body 26, the stem 52 and thus collet assembly 64 moves forward within the interior of the body 26 and the conical tip 28. As the split chuck 68 moves forward, the ferrule 62 also moves forward until the forward edge of the ferrule contacts a shoulder 74 formed in the interior of the cylindrical cavity 70, thus preventing the ferrule from moving forward any further. As the split chuck 68 continues to move forward, the jaws 70 move out of the ferrule 62 allowing the jaws to move radially apart, thus increasing the diameter of the passageway 72. As the diameter of the passageway 72 increases, the needle electrode 18 is free to move into or out of the needle electrode holder 16.

A needle electrode 18 may be inserted into the needle electrode holder 16 while the base 24 is depressed by inserting it through the conical opening 38 into the split chuck 68. The conical opening 38 helps to guide the needle electrode in the passageway 72. The base 24 may then be released allowing the biasing force of the spring 60 to force the base rearwardly, thus compressing the jaws 70 around the needle electrode as described above.

In the preferred embodiment, the stem 52 and collet assembly 64 are formed of an electrically conductive material. A conductor 91 that forms part of the electrical lead 14 is attached to the rear portion of the stem 52 by crimping, soldering, or other means of attachment, thus establishing an electrical path from the lead to the needle electrode 18.

In operation, the user inserts a needle electrode by depressing the base 24 (i.e., moving the base 24 toward the body 26), sliding a needle electrode 18 into the tip 28 and releasing the base 24. To dispose of a used needle electrode 18, the user holds the needle electrode 18 and needle electrode holder 16 over a disposal receptacle and depresses the base 24, allowing the needle electrode 18 to fall into the disposal receptacle.

The present invention allows various diameters, lengths, and types of needle electrodes to be used within a standard needle electrode holder. A physician may stock the present invention along with a large variety of needle electrodes as opposed to stocking a large quantity of various sizes and lengths of disposable needle electrode assemblies, thus reducing storage and overhead costs. The present invention may also be reused, thereby reducing medical waste and disposal costs.

If the needle electrode holder 16 is contaminated by a patient's bodily fluids, it may be sterilized using commonly known and used sterilization procedures. The present invention may be used with either monopolar or dipolar needle electrodes by making minor electrical modifications as readily accomplished by someone of ordinary skill in the art.

The present invention may be used with needle electrodes of varying sizes, lengths, and configurations; however, it is advantageous to use the present invention with a needle electrode 18 that includes a stand-off section 100 designed to off-set the tip 28 of the needle electrode from a patient's body. The stand-off section 100 shown in FIG. 2 is a Z-shaped bend in the needle electrode 18. The distal portion 102 of the Z-shaped bend contacts a patient's skin and prevents the needle electrode 18 from being inserted beyond a predetermined position. The proximal portion 104 of the Z-shaped bend contacts the tip 28 of the needle electrode holder once the needle electrode 18 is fully inserted into the needle electrode holder. Using a needle electrode having a stand-off section 100 as shown helps to prevent the needle electrode holder from becoming contaminated by contact with the surface of a patient's body or the patient's bodily fluids.

While the preferred embodiment of the invention has been illustrated and described, it will be appreciated that, within the scope-of the appended claims, various changes can be made therein without departing from the spirit and scope of the invention.

The embodiments of the invention in which an exclusive property or privilege is claimed are defined as follows:

1. A needle electrode assembly including a holder for releasably holding a needle electrode, the assembly comprising:
   an electrical connector;
   an electrical lead having one end connected to said electrical connector; and
   a needle electrode holder including:
   a body;
   a base slidably mounted in the body; and
   a chuck formed of an electrically conducting material having at least two jaws mounted in one end of the body and mechanically coupled to the base and electrically connected to the other end of said electrical lead, the jaws forming an opening sized to receive and releasably hold a needle electrode, the chuck being movable from an engaged position in which the jaws engage and hold the needle electrode to a released position in which the needle electrode may move freely out of the chuck when the base is slidably moved with respect to the body.

2. The electrode assembly of claim 1, further comprising biasing means for biasing the chuck into the engaged position.

3. The electrode assembly of claim 2, further comprising a ferrule at least partially encircling the chuck and wherein the biasing means biases the chuck into contact with the ferrule when the chuck is in the engaged position.

4. The electrode assembly of claim 1, further comprising a ferrule at least partially encircling the chuck so that when the base is slidably moved with respect to the body, the chuck moves at least partially into and out of the ferrule to move the chuck from the engaged position to the released position.

5. The electrode assembly of claim 1, wherein the chuck includes a tube having a split end that forms the jaws and wherein the jaws move radially inward and outward to enlarge and reduce the size of the opening to engage and release the needle electrode.

6. The electrode assembly of claim 1, wherein the body has a concave contour that receives and is held between two fingers of a user's hand and the base is located at one end of the body and is operated by the thumb of the user's hand.

7. The electrode assembly of claim 1, wherein the base is slidably mounted in an end of the holder opposite the chuck.

8. The electrode assembly of claim 1, wherein the holder further comprises a tip coupled to one end of the body, the tip including a conical opening adapted to guide the needle electrode into the opening in the chuck.

9. A reusable needle electrode assembly comprising:
   an electrical lead;
   an electrical connector attached to one end of the electrical lead, the electrical connector being used to electrically attach the needle electrode assembly to monitoring equipment; and
   a needle electrode holder attached to an opposite end of the electrical lead, the needle electrode holder including:
   a body having opposing ends;
   a base slidably mounted in an opening in one end of the body; and
   a chuck including at least two opposing jaws, the chuck being slidably mounted in the opposite end of the body and connected to the base, the jaws being formed of an electrically conductive material and being electrically connected to the electrical lead and forming a centrally located opening sized to receive and releasably hold a needle electrode, the chuck being slidably movable from an engaged position in which the jaws move radially inward to engage and hold the needle electrode to a released position in which the needle electrode may move freely out of the chuck when the base is depressed into the opening in the body.

10. The assembly of claim 9, further comprising means for biasing the chuck into the engaged position.

11. The assembly of claim 9, further comprising a ferrule at least partially encircling the chuck so that depressing the base into the opening in the body causes the jaws to move out of the ferrule and expand radially outward to disengage from the needle electrode.

12. The assembly of claim 9, wherein the body includes a concave countour that receives and is held between two fingers of a user's hand and the base is operated by the thumb of the user's hand.

13. The assembly of claim 9, wherein the body includes a conically shaped opening adjacent the chuck to guide the needle electrode into the jaws of the chuck.

14. A combination of a needle electrode assembly and a needle electrode, the combination comprising:
   a needle electrode including a stand-off mechanism that prevents the needle electrode assembly from contacting a patient's bodily fluids when the needle electrode is inserted into a patient;
   a needle electrode assembly including;
   a body;
   a base movably coupled to the body; and
   a gripping assembly mounted in the body and coupled to the base, the gripping assembly being movable between an engaged position in which the gripping assembly engages and holds the stand-off mechanism of the needle electrode and a released position in which the gripping assembly allows the stand-off mechanism to move freely into and out of the gripping assembly, wherein moving the base with respect to the body causes the gripping assembly to move between the engaged position and the released position.

15. The combination of claim 14, further comprising biasing means for biasing the gripping assembly into the engaged position.

16. The combination of claim 15, wherein the gripping assembly includes a chuck having at least two jaws that move radially inward and outward to engage and disengage the stand-off mechanism of the needle electrode.

17. The combination of claim 16, further comprising a ferrule at least partially encircling the jaws and wherein movement of the ferrule with respect to the jaws causes the ferrule to compress or release the jaws causing the gripping assembly to move between the engaged position and the released position.

18. The combination of claim 14, wherein the body is contoured to receive and be held by two fingers of the user's hand and the base is located at one end of the body and is operated by the thumb of the user's hand.

19. The combination of claim 14, wherein the body includes a conically shaped opening that guides the stand-off mechanism inserted into the needle electrode assembly into the gripping assembly.

* * * * *